(12) United States Patent
Tyrrell

(10) Patent No.: US 6,187,531 B1
(45) Date of Patent: *Feb. 13, 2001

(54) METHOD FOR CORRECTING FOR BLOOD VOLUME IN A SERUM ANALYTE DETERMINATION

(75) Inventor: Steven P. Tyrrell, Highland Park, IL (US)

(73) Assignee: Biosafe Medical Technologies, Inc., Lincolnshire, IL (US)

(*) Notice: Under 35 U.S.C. 154(b), the term of this patent shall be extended for 0 days.

This patent is subject to a terminal disclaimer.

(21) Appl. No.: 09/481,274

(22) Filed: Jan. 11, 2000

Related U.S. Application Data

(63) Continuation of application No. 09/264,169, filed on Mar. 5, 1999, now Pat. No. 6,040,135.
(60) Provisional application No. 60/077,030, filed on Mar. 6, 1998.

(51) Int. Cl.[7] .............................. C12Q 1/00; C12Q 1/60; C12Q 1/37; G01N 31/00
(52) U.S. Cl. .................... 435/4; 435/11; 435/23; 435/40.5; 435/283.1; 435/805; 436/15
(58) Field of Search ................... 435/4, 11, 23, 435/40.5, 283.1, 805; 436/15

(56) References Cited

U.S. PATENT DOCUMENTS

| | | | |
|---|---|---|---|
| 5,122,451 | 6/1992 | Tanaka et al. | 435/4 |
| 5,788,942 | 8/1998 | Kitani et al. | 435/4 |
| 6,040,135 | * 3/2000 | Tyrrell | 435/4 |

* cited by examiner

Primary Examiner—Louise N. Leary
(74) Attorney, Agent, or Firm—Brinks Hofer Gilson & Lione

(57) ABSTRACT

This invention relates to the measurement of analytes in dried blood samples. It has been discovered by measuring the hemoglobin in the dissolved dried blood sample, an estimate of blood volume may be made and used to make a correction for blood volume. Thus, analytes such as cholesterol, PSA, and other blood analytes can be more accurately determined. The invention further describes a blood collection device and disk material on which blood is dried to provide superior results.

15 Claims, 2 Drawing Sheets

FIGURE 2

| Serum Cholesterol (mg/dl) | Hematocrit Correction DBS Cholesterol (mg/dl) | No Hematrocrit Correction DBS Cholesterol (mg/dl) |
|---|---|---|
| 158 | 150 | 130 |
| 203 | 188 | 187 |
| 210 | 216 | 207 |
| 197 | 215 | 196 |
| 184 | 188 | 170 |
| 187.5 | 172 | 169 |
| 160 | 170 | 165 |
| 156.5 | 168 | 174 |
| 203.5 | 192 | 192 |
| 158.5 | 146 | 153 |
| 205.5 | 186 | 187 |
| 200 | 179 | 176 |
| 165 | 166 | 179 |
| 215.5 | 216 | 220 |
| 168 | 161 | 176 |
| 195.5 | 213 | 216 |
| 202 | 210 | 220 |
| 338 | 343 | 360 |
| 192 | 188 | 180 |
| 190.5 | 183 | 201 |
| 250.5 | 236 | 239 |
| 179.5 | 173 | 195 |
| 216.5 | 208 | 202 |
| 193.5 | 176 | 175 |
| 144.5 | 145 | 154 |
| 187.5 | 188 | 181 |
| 222.5 | 222 | 204 |
| 168 | 165 | 180 |
| 210 | 201 | 197 |
| 252 | 249 | 260 |
| 179.5 | 161 | 152 |
| 101 | 111 | 114 |
| 228 | 225 | 216 |
| 192 | 210 | 195 |
| 191.5 | 218 | 211 |
| 174 | 192 | 180 |
| 249.5 | 283 | 277 |
| 168.5 | 195 | 206 |
| 206.5 | 220 | 220 |

METHOD FOR CORRECTING FOR BLOOD VOLUME IN A SERUM ANALYTE DETERMINATION

CROSS-REFERENCE

This application is a continuation of Ser. No. 09/264,169 filed Mar. 5, 1999, now U.S. Pat. No. 6,040,135 which is a continuation of provisional application Ser. No. 60/077,030, filed Mar. 6, 1998.

FIELD OF THE INVENTION

The present invention is directed generally to the field of blood analyte assay systems in which a hematocrit is used to calculate the serum concentration of the analyte, and more particularly relates to a method for quantifying the amount of cholesterol in dried blood samples.

BACKGROUND OF THE INVENTION

Methods for determining the concentration of serum constituents are indispensable for the diagnosis and treatment of clinical conditions. The volume of plasma must be known when quantitating the concentration of a serum constituent. The volume of red blood cells present in blood (hematocrit) in universally proportional to the volume of plasma. The hematocrit, however, varies significantly from person to person posing a problem when analyzing whole blood for plasma (serum) chemistries. The present invention describes an unexpected way of overcoming this difficulty. It is widely recognized that in otherwise healthy individuals, hematocrit is directly proportional to total hemoglobin. Hemoglobin determinations are more consistent and accurate than hematocrit determinations. Thus the present invention permits the measurement accurate calculation of the concentration of the serum constituent being measured from a dried blood sample.

Another object of the invention is to provide an assay for blood analytes such as cholesterol and prostate specific antigen (PSA) which obviates the need for a hematocrit determination.

These and other objects of the invention would be apparent in light of the detailed description below.

SUMMARY OF THE INVENTION

The present invention relates to a method for determining plasma volume from dried blood samples where the dried blood sample is eluted and the cholesterol and hemoglobin levels are measured. It has been discovered that the hematocrit correction in measuring serum constitutent concentrations in fresh blood samples can be achieved from measuring hemoglobin from the dried blood sample and applying a correction factor based on the hemoglobin level. A blood collection and drying device and preferred materials on which blood is dried is described.

These and other features and advantages of the present invention may be better understood by considering the following detailed description of certain preferred embodiments of the invention. In the course of this description, reference will be made to the attached drawings.

BRIEF DESCRIPTION OF THE DRAWINGS

Various objects, features and attendant advantages of the present invention can be more fully appreciated as the same become better understood with reference to the following detailed description of the present invention when considered in connection with the accompanying drawings in which:

FIG. 2 is representative comparative hematocrit corrected versus non-corrected dried blood sample (DBS) cholesterol values.

DETAILED DESCRIPTION OF PRESENTLY PREFERRED EMBODIMENTS

Blood Collection for Dried Blood

Figure 1A:
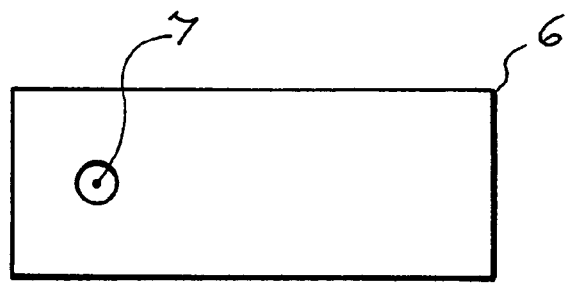
FIGS. 1(a), (b) and (c) describe component parts of a device for collecting and drying blood samples.

Those skilled in the clinical chemistry arts will recognize a large number of devices for collecting blood samples and shipping dried blood samples. A preferred device for collecting and drying blood sample is illustrated in FIGS. 1a, b, c and d.

Figure 1B:
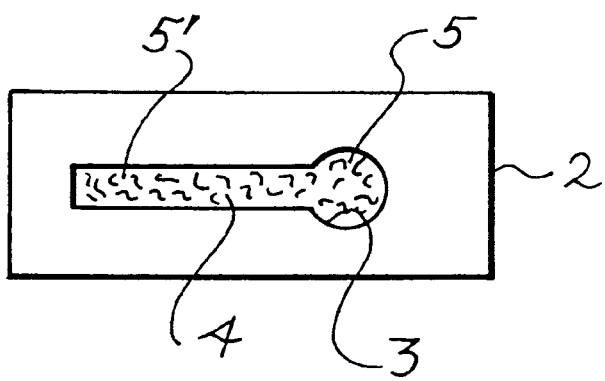
FIG. 1(d) is a cross sectional view of the assembled blood collection device.
Figure 1C:
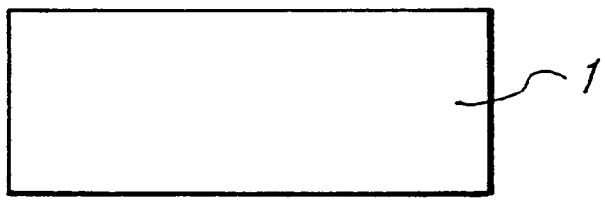
Figure 1D:
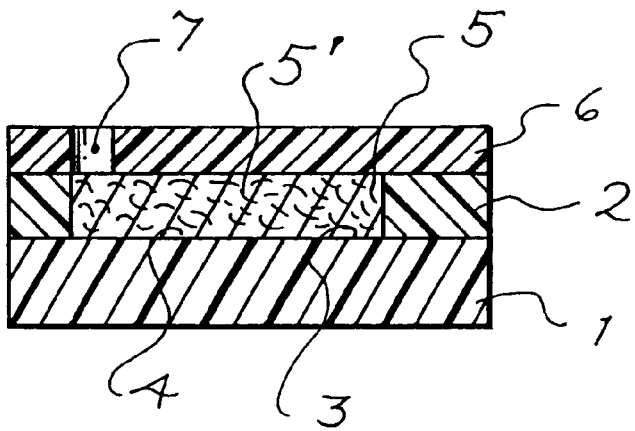

FIG. 1(c) is a base plate. FIG. 1(b) shows a middle plate 2 with which defines an opening 3 and a lateral channel 4. This lateral channel 4 may be filled with a strip 5', made of a hydrophilic material which will absorb liquid to ensure that there is a uniform amount of blood on sample disk 5 which fits into 3. FIG. 1(a) is a top plate 6 having a hole 7. The plates shown as FIG. 1(c), FIGS. 1(a) and 2 are made of a hydrophobic plastic material. The plates are assembled by stacking and blood is introduced into hole 7 and is absorbed into disk 5 via strip 5'. FIGS. 1(a), 1(b), 1(c) are made of a hydrophobic plastic that permits the drying of blood absorbed into disk 5. When disk 5 is completely dry, Disk 5 is removed and the dried blood sample is eluted and analyzed. FIG. 1(d) is a cross sectional view of the assembled device.

Those skilled in the clinical chemistry arts will recognize a wide variety of porous materials useable as a disk for dried blood sample. Schleicher & Schuell 903 collection paper (Exhibit C) is suitable for analysis of dried blood samples. A preferred porous medium is Porex® Plastics 70 $\mu$m Lateral-Flow™ X-4588 (Exhibit D). This medium is a hydrophilic plastic material high density polyethylene with a pore diameter of about 0.1 to 2$\mu$. This material provides very significant advantages in providing a uniform dried blood sample for more accurate analysis.

Those skilled in the clinical chemistry arts will recognized a wide variety of hydrophobic plastic that permits the drying of the dried blood sample inside the assembled device. A preferred hydrophobic plastic material is Porex® Plastics 7774 7 $\mu$m product. This material provides very significant advantages in providing a uniform dried blood sample for more accurate analysis.

Elution of the Dried Blood Sample

The dried blood sample may be eluted using a number of eluents known to those skilled in the art. The preferred eluent for achieving precise and complete elution is a 0.5 mole/liter sodium chloride solution containing 0.25% (Vol./Vol.) nonoxynol, a nonionic detergent. Four dried blood spots that are ⅛ in diameter are placed into a single well of a polystyrene microplate, such as the Millipore Multiscreen® microplate. A small volume of the eluting reagent, 100 $\mu$l, is added and the system is shaken at 1000 rpm for one hour. The Multiscreen microplate is equipped with a filtration membrane at the bottom of the microwell which, when centrifuged (1350×g for 10 minutes) causes all liquid to be pushed through the membrane to be collected below, permitting complete extraction of blood from the filter packet disks.

Hemoglobin Assay Procedure

The present invention measures total hemoglobin in the dried blood spot using Drabkins Reagent on each dried blood sample to be analyzed for total cholesterol. The total hemoglobin assay is calibrated by using a concentrated Sigma hemoglobin standard (1 vial Cat. # 525-1B with 2.67 ml of Drabkins reagent added).

Cholesterol Assay Procedure

Preferably, testing is performed on an autoanalyzer (Beckman CX-7). A commercially available reagent for total cholesterol (Synermed IR060) has been adapted for use in whole blood. The two parts of the reagent are normally mixed together and used as a single part. The reagent is now being used as a two-part system. The autoanalyzer adds one part of the reagent to the specimen and spectrophotmetrically reads the absorbance of the solution effectively "blanking" out the variable absorbance of the endogenous hemoglobin. Once blanking is complete, the second part of the cholesterol reagent is added and the reagent system produces a signal proportional to the amount of cholesterol present in the system. The total cholesterol assay is calibrated by diluting the provided serum standard 1:8.67 in eluting reagent.

Summary of Calculation

When analysis is complete, a calculation is performed which converts the dried blood cholesterol and total hemoglobin value versus the diluted wet blood standards to the corresponding serum cholesterol value. The relationship to total hemoglobin extracted from whole blood spotted onto Schleicher & Schuell 903 collection paper (Exhibit C) to dried blood total cholesterol (extracted from the same sample) deviance from serum cholesterol has been statistically determined and has been shown to improve the accuracy of dried blood cholesterol analysis. The relationship is programmed into the autoanalyzer and the final total cholesterol result is calculated from both the hemoglobin and dried blood cholesterol result. The serum cholesterol is equal to the formula: $((DCHL \times (1+(0.45 \times ((DHGB/18)-1))))-0.86)/0.04$. The term DCHL is the value of the total cholesterol determined from the dried blood sample assay (DBS Cholesterol). The term DHGB is the hemoglobin value determined from the dried blood sample assay (DBS Hemoglobin value). The above formula is two relationships combined into one formula. The relationship of DBS Cholesterol to the diluted Serum Cholesterol Calibrator is: Serum Cholesterol=$(DHGB-0.86)/0.04$. The relationship of DBS Hemoglobin to DBS Cholesterol hematocrit variation is: Correction Factor=$(0.45 \times (DHGB/Average\ Hemoglobin)-1)$. Where the average DBS hemoglobin has been determined to be 18 mg/dl versus the Sigma® calibrator prepared as described. All unspecified units are in mg/dl.

FIG. 2 is a table of three columns of assays comparing the results achieved with the whole blood cholesterol assay corrected with a hematocrit (left hand column), results achieved with the dried blood sample (DBS) assay for cholesterol corrected for with the hemoglobin estimate of the hematocrit (middle column) and the results achieved with the dried blood sample (DBS) assay for cholesterol where the hematocrit is not measured or estimated (far right column).

Representative detailed procedures for measuring cholesterol and hemoglobin are attached as Exhibits A and B, respectively. Those skilled in the clinical diagnostic arts will be aware of a variety of methods for measuring cholesterol and hemoglobin levels.

Prostate Specific Antigen Assay Procedure

The measurement of PSA in dried blood in conjunction with digital rectal exam (DRE) is useful as an aid in the detection of prostate cancer in men aged 50 years or older. The sample of choice for this procedure is capillary whole blood collected on filter paper. It takes approximately 50 ul of blood to fill a single circle on the collection card. The optimum sample is a blood collection card with three completely filled circles. The minimum specimen requirement is five ⅛-inch diameter spots from any of the circles of the blood collection card. The acceptable "specimen container" is a blood collection card made of Schleicher & Schuell 903 collection paper, described herein. The specimen is stable for weeks when stored in a desiccated environment at room temperature. An unacceptable specimen will have less than five ⅛-inch diameter spots from any of the 3 circles on the blood collection card.

Physical characteristics of the specimen that can comprise the test results include: (1) Incompletely filled blood collection circles; (2) blood not soaked completely through the collection card; (3) An incompletely dried card. The specimen may be collected at any time. After collection, allow the blood collection card to air dry in a clean, dry area for at least three hours. If possible, the card is allowed to dry in a safe place overnight. The blood collection card should not be exposed to direct sunlight or extreme temperature or humidity. When the blood collection card is completely dry, it is inserted into the blood collection card envelope. The completed laboratory authorization form and envelope (with blood collection card enclosed) is mailed to the laboratory for testing.

The dried blood samples are eluted according to the procedure detailed above (see Elution of dried blood sample). The sample is assayed for PSA using a kit made by Hybridtech, the Tandem®-MP PSA assay. The assay is a solid phase, two-site immunoenzymetric assay. Samples containing Prostate specific assay (PSA) are reacted with a solution containing two PSA-specific monoclonal antibodies. One is alkaline phosphatase-labeled; the other is biotin-labeled. The reaction takes place in the plastic microplate (solid phase) consisting of a frame and several strips of wells coated with stepavidin (which binds with biotin). Following the formation of a solid phase/capture antibody/PSA/Labeled antibody sandwich, the microplate is washed to remove unbound-labeled antibody and is then incubated with an enzyme substrate. The amount of substrate turnover is determined colormetrically by measuring the absorbance of the quenched reaction at 450 nm in a microplate reader. The absorbance is proportional to the concentration of PSA present in the test sample.

For further details on the Hybridtech Tandem®-MP PSA assay the reader is directed to U.S. Pat. Nos. 4,486,530 and 4,376,110.

Those skilled in the clinical chemistry arts will recognized that in addition to the assay method disclosed for PSA, there are other methods for assaying for PSA such as disclosed in Hoffman et al., (1996) *Clinical Chemistry*, 42: 536–544.

The method of this invention used to assay for cholesterol and PSA are equally applicable to the determination of other blood analytes that require a hematocrit determination.

What is claimed is:

1. A method of determining the concentration of an analyte in a blood sample, comprising:

determining the hematocrit of the blood sample; and determining the amount of the analyte in the blood sample;

wherein the blood sample is dried blood.

2. The method of claim 1, further comprising, before the measuring:

collecting and drying the blood sample on a porous material; and eluting the blood sample from the porous material.

3. A method of determining the concentration of an analyte in a blood sample, comprising:

measuring the amount hemoglobin in the blood sample; and determining the amount of the analyte in the blood sample;

wherein the analyte is selected from the group consisting of cholesterol and prostate specific antigen.

4. The method of claim 3, further comprising, before the measuring:

collecting and drying the blood sample on a porous material; and eluting the blood sample from the porous material.

5. A method of determining the serum volume of a dried blood sample, comprising:

measuring the amount of hemoglobin in the blood sample.

6. A method of determining the concentration of an analyte in a blood sample, comprising:

measuring the amount hemoglobin in the blood sample;

determining the amount of the analyte in the blood sample; and calculating the concentration of the analyte in the blood sample.

7. The method of claim 6, further comprising, before the measuring:

collecting and drying the blood sample on a porous material; and eluting the blood sample from the porous material.

8. A method of determining the concentration of an analyte in a blood sample, comprising:

(a) mailing the blood sample;

(b) determining the hematocrit of the blood sample; and (c) determining the amount of the analyte in the blood sample.

9. The method of claim 8, further comprising, prior to the mailing, drying the blood sample.

10. The method of claim 8, wherein the analyte is prostate specific antigen.

11. A method of determining the concentration of an analyte in a blood sample, comprising:

(a) mailing the blood sample;

(b) measuring the amount hemoglobin in the blood sample; and (c) determining the amount of the analyte in the blood sample.

12. The method of claim 11, further comprising, prior to the mailing, drying the blood sample.

13. The method of claim 11, wherein the analyte is prostate specific antigen.

14. The method of claim 8 wherein (b) and (c) are performed after (a).

15. The method of claim 11 wherein (b) and (c) are performed after (a).

* * * * *